(12) United States Patent
Yang et al.

(10) Patent No.: US 11,619,627 B2
(45) Date of Patent: Apr. 4, 2023

(54) PENCIL-LIKE OPTICAL FIBER SENSOR PROBE, PORTABLE IMMUNOSENSOR AND USE THEREOF

(71) Applicants: Northeast Normal University, Jilin (CN); Changchun JingKeOuDe Science and Education Instrument Co., Ltd., Jilin (CN)

(72) Inventors: Li Yang, Jilin (CN); Rongbin Nie, Jilin (CN); Yunxiang Feng, Jilin (CN); Chengwei Feng, Jilin (CN)

(73) Assignees: Northeast Normal University, Changchun (CN); Changchun JingKeOuDe Science and Education Instrument Co., Ltd., Changchun (CN)

( * ) Notice: Subject to any disclaimer, the term of this patent is extended or adjusted under 35 U.S.C. 154(b) by 530 days.

(21) Appl. No.: 16/827,231

(22) Filed: Mar. 23, 2020

(65) Prior Publication Data
US 2021/0123908 A1    Apr. 29, 2021

(51) Int. Cl.
*G01N 33/68* (2006.01)
*G01N 33/53* (2006.01)

(52) U.S. Cl.
CPC ..... *G01N 33/5302* (2013.01); *G01N 33/6869* (2013.01); *G01N 33/6893* (2013.01); *G01N 2333/4737* (2013.01); *G01N 2333/5412* (2013.01)

(58) Field of Classification Search
CPC .................................................. G01N 33/5302
See application file for complete search history.

(56) References Cited

U.S. PATENT DOCUMENTS 4,624,243 A * 11/1986 Lowery .............. A61B 1/00165
                                                              600/114
5,082,630 A *  1/1992 Partin ................ G01N 33/9486
                                                              436/527

FOREIGN PATENT DOCUMENTS

CN         106290896 A     1/2017
CN         108931647 A    12/2018

* cited by examiner

*Primary Examiner* — Jennifer Wecker
*Assistant Examiner* — Mickey Huang (57) ABSTRACT

The present invention discloses a pencil-like optical fiber sensor probe, including an inner tube, a light screening casing, a clamping device, an optical fiber and an optical probe; a portable immunosensor, including the pencil-like optical fiber sensor probe, an immersion immune response reagent strip, a touch-screen computer, a compact battery-powered sensitive photon counting detector and a case; and a use of the immunosens in detecting inflammatory markers. The design of the pencil-like optical sensor probe greatly simplifies the immune analysis process by combining the immersion immune response reagent strip. Each optical probe allows for up to 10 immunoassays, which reduces the experimental cost and avoids frequent replacement of the probe. The integrated detecting system is powered by battery which is suitable for in-situ analysis and detection. The sensor also has a high stability and sensitivity.

8 Claims, 11 Drawing Sheets

PENCIL-LIKE OPTICAL FIBER SENSOR PROBE, PORTABLE IMMUNOSENSOR AND USE THEREOF

CROSS-REFERENCE TO RELATED APPLICATIONS

This application claims the benefit of priority from Chinese Patent Application No. 201911021355.8, filed on Oct. 25, 2019. The content of the aforementioned application, including any intervening amendments thereto, is incorporated herein by reference in its entirety.

TECHNICAL FIELD

This application relates to disease marker analysis, and more particularly to a pencil-like optical fiber sensor probe, a portable immunosensor and a use thereof.

BACKGROUND OF THE INVENTION

Analysis and detection for disease-specific biomarkers are essential for early diagnosis and screening of diseases, and in the monitoring of treatment effect. Currently, the clinical detection for biomarkers are mainly implemented by large-scale equipment in medical institutions. The detecting process is complicated and requires professional personnel. Compared with the clinical analysis methods, portable and user-friendly diagnostic tools, used for point-of-care testing (POCT), are capable of detecting disease markers without laboratory equipment and professional operations. In recent years, immunosensors are developed for the transition from laboratory analysis to POCT. The immunosensor combines the advantages of traditional immunoassay and biosensing technology, having great prominence in the determination of biomarkers, especially in the sensitive detection of antigens and antibodies.

Based on different physical and chemical mechanisms, researchers have developed various immunosensors, such as quartz crystal sensors, electrochemical sensors, pressure-based sensors, for quantitative analysis of immune molecules. Chemiluminescent optical fiber immunosensors is welcomed due to the small size and strong anti-interference ability thereof and being easy to handle. The chemiluminescent optical fiber immunosensor directly converts immune recognition into luminescent signals, and excitation light sources and spectrometers are eliminated. In addition, it has a high sensitivity to avoid the interference from external environment. So portable analyzers can be constructed based on the chemiluminescent optical fiber immunosensor for POCT. However, liquid control systems for the immune response and charge coupled devices (CCD) for signal acquisition are required for most traditional chemiluminescent immunosensors, resulting in a higher cost and complicated structure, which limits the miniaturization, integration and portability of the analyzer. Therefore, it is of great significance for POCT to construct a chemiluminescent optical fiber immunosensor which has integrated functions, easy operations and a small size, and is portable. Moreover, there is no report over chemiluminescent pencil-like optical fiber immunosensors for detecting disease markers.

SUMMARY OF THE INVENTION

In order to overcome the problems of complicated analyzing operations and long detection time for disease markers, the present invention aims to provide a pencil-like fiber sensor probe and a portable immunosensor which are reusable and stable, and can be used for POCT.

The present invention provides a pencil-like optical fiber sensor probe, comprising:
an inner tube;
a casing;
a clamping device;
an optical fiber; and
an optical probe;
wherein the inner tube comprises a head, a screw cylinder and a tail cap; a fixing part is provided at an upper end of the screw cylinder, and a guide groove is provided on a sidewall of the screw cylinder; and the tail cap is fixed to the fixing part;
the casing is sheathed on the screw cylinder, and a helix groove is provided on an inner wall of the casing;
the clamping device is arranged in the screw cylinder;
the optical fiber and the optical probe are coaxially connected in the clamping device, so that light is guided from the optical probe to the optical fiber to the maximum;
the casing is made of a light screening material;
the clamping device comprises a helix slider, a receiving slider and a mechanical splicer; the helix slider and the receiving slider are connected in a snap fit; the mechanical splicer is arranged in the connected helix slider and the receiving slider; and a protrusion is provided on an outer wall of the helix slider;
a first clamping part is provided at a lower end of the helix slider, and a second clamping part is provided at an upper end of the receiving slider;
the protrusion slides into the guide groove, and then is embedded into the helix groove; the protrusion slides up and down along the guide groove to extend or retract the optical probe;
two guide grooves are axisymmetrically arranged on the sidewall of the screw cylinder;
the optical probe is modified by capture antibodies.

The present invention further provides a portable immunosensor, comprising the pencil-like optical fiber sensor probe, an immersion immune response reagent strip, a screen-touch computer, a compact battery-powered sensitive photon counting detector and a case; the pencil-like optical fiber sensor probe, the immersion immune response reagent strip, the screen-touch computer and the compact battery-powered sensitive photon counting detector are arranged in the case; the pencil-like optical fiber sensor probe, the compact battery-powered sensitive photon counting detector and the screen-touch computer are sequentially connected; and the compact battery-powered sensitive photon counting detector is arranged in a dark place;
the pencil-like optical fiber sensor probe, the immersion immune response reagent strip and the touch-screen computer are installed at an upper layer of the case, and the compact battery-powered sensitive photon counting detector is sealed at the dark place located on a bottom of the case.

The portable immunosensor is applied for detecting an inflammatory marker.

The inflammatory marker is interleukin-6, procalcitonin and/or C-reactive protein.

The present invention provides the pencil-like optical sensor probe, which comprises the inner tube, the casing, the clamping device, the optical fiber and the optical probe. The present invention further provides the portable immunosensor which comprises the pencil-like optical sensor probe, the immersion immune response reagent strip, the touch-screen computer and the compact battery-powered sensitive photon counting detector and the case. The portable immunosensor is used to detect inflammatory markers. The design of the pencil-like optical sensor probe greatly simplifies the immune analysis process by combining the immersion immune response reagent strip. Each optical probe allows for up to 10 immunoassays, which reduces the experimental cost and avoids frequent replacement of the probe. The integrated detecting system is powered by battery which is suitable for in-situ analysis and detection. The sensor also has a high stability and sensitivity.

DETAILED DESCRIPTION OF EMBODIMENTS

Example 1

Figure 6:
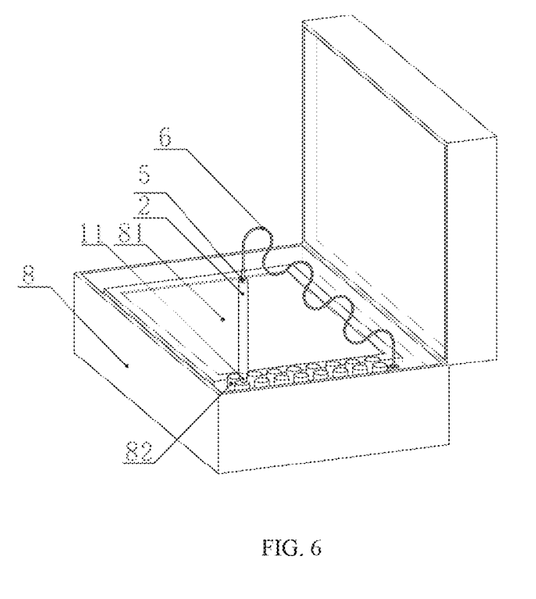
FIG. 6 is a schematic diagram of a case (PPS platform) of the portable immunosensor of the present invention.

In this embodiment, as shown in FIG. 6, illustrated is a portable immunosensor, comprising a pencil-like optical fiber sensor probe, an immersion immune response reagent strip 82, a touch-screen computer 81, a compact battery-powered sensitive photon counting detector and a case 8. The pencil-like optical fiber sensor probe, the immersion immune response reagent strip, the touch-screen computer and the compact battery-powered sensitive photon counting detector are arranged in the case. The pencil-like optical fiber sensor probe, the compact battery-powered sensitive photon counting detector and the touch-screen computer are sequentially connected. The compact battery-powered sensitive photon counting detector is arranged in a dark place.

The pencil-like optical fiber sensor probe, the immersion immune response reagent strip and the touch-screen computer are arranged at an upper layer of the case; and the compact battery-powered sensitive photon counting detector is sealed at the dark place located on a bottom of the case.

The compact battery-powered sensitive photon counting detector located at the dark lower layer of the case is constructed based on commercial photon counters of Beijing HamamatsuPhoton Techniques INC. A chemiluminescent output signal of the immune response is generated by the pencil-like optical fiber sensor probe, and then is transmitted to the compact battery-powered sensitive photon counting detector via a flexible optical fiber, and is finally collected and processed by the screen-touch computer.

The present invention further provides a portable immunosensor (PPS) which is assembled in the case, so that it is convenient to carry out the point-of-care testing for the disease markers. The portable immunosensor comprises the pencil-like optical fiber sensor probe, the immersion immune response reagent strip, the screen-touch computer, and the compact battery-powered sensitive photon counting detector. The pencil-like optical fiber sensor probe, the immersion immune response reagent strip and the touch-screen computer are arranged at an upper layer of the case, and the compact battery-powered sensitive photon counting detector is sealed at the bottom of the case to avoid the interference of ambient light. The portable immunosensor has a size of 32 cm*23 cm*11 cm, and the weight thereof is only 3 kg.

Example 2

Figure 1:
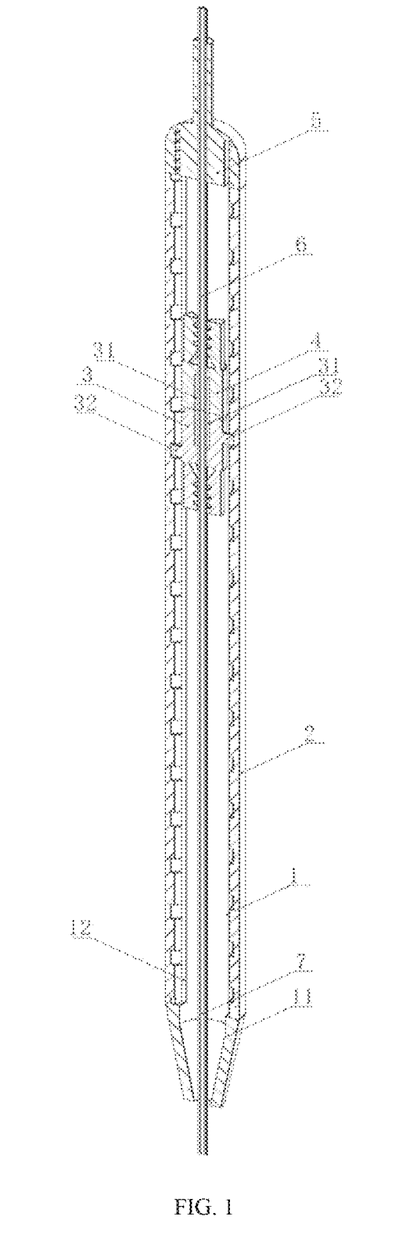
FIG. 1 is a sectional view of a portable immunosensor of the present invention.
Figure 2:
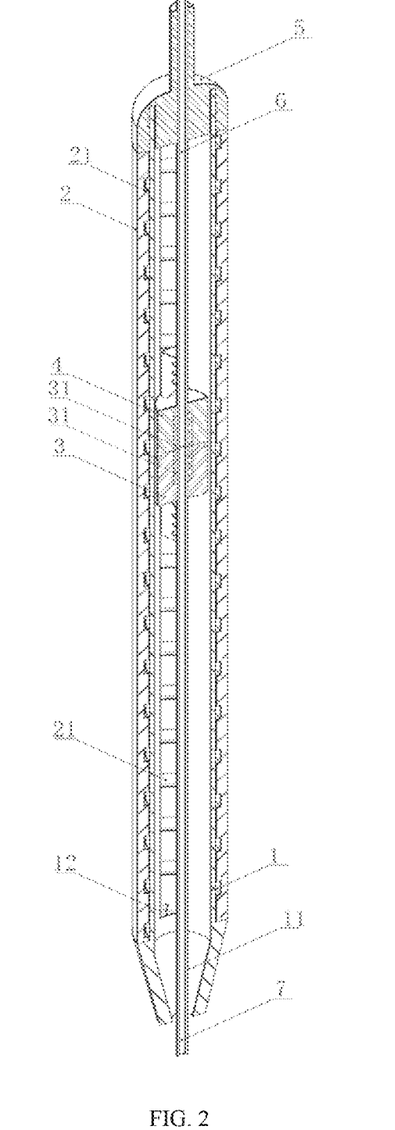
FIG. 2 is another sectional view of the portable immunosensor of the present invention.
Figure 3:
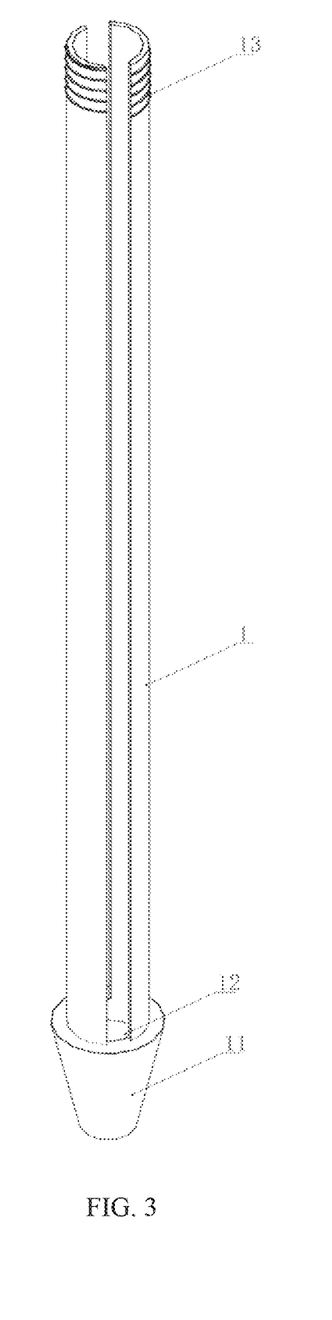
FIG. 3 is a schematic diagram of an inner tube of the portable immunosensor of the present invention.

As shown in FIGS. 1-3, illustrated is a pencil-like optical fiber sensor probe, comprising an inner tube, a casing 2, a clamping device, an optical fiber 6 and an optical probe 7.

The inner tube comprises a head 11, a screw cylinder 1 and a tail cap 5; a fixing part 13 is provided at an upper end of the screw cylinder 1; a guide groove 12 is arranged on a sidewall of the screw cylinder; and the tail cap 5 is fixed to the fixing part 13.

Figure 4:
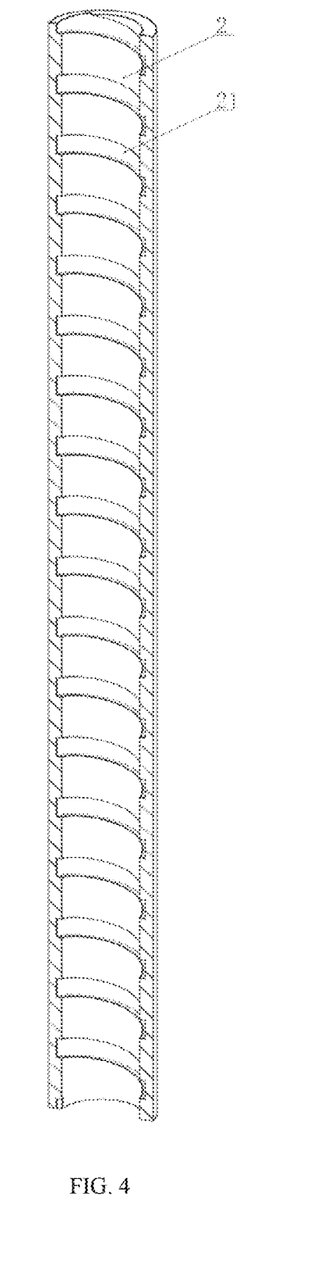
FIG. 4 is a sectional view of a casing of the portable immunosensor of the present invention.

The casing 2 is sheathed on the screw cylinder 1, and as shown in FIG. 4, a helix groove 21 is provided on an inner wall of the casing 2.

The clamping device is arranged inside the screw cylinder 1.

The optical fiber 6 and the optical probe 7 are coaxially connected in the clamping device, so that light is guided from the optical probe 7 to the optical fiber 6 to the maximum.

Figure 5:
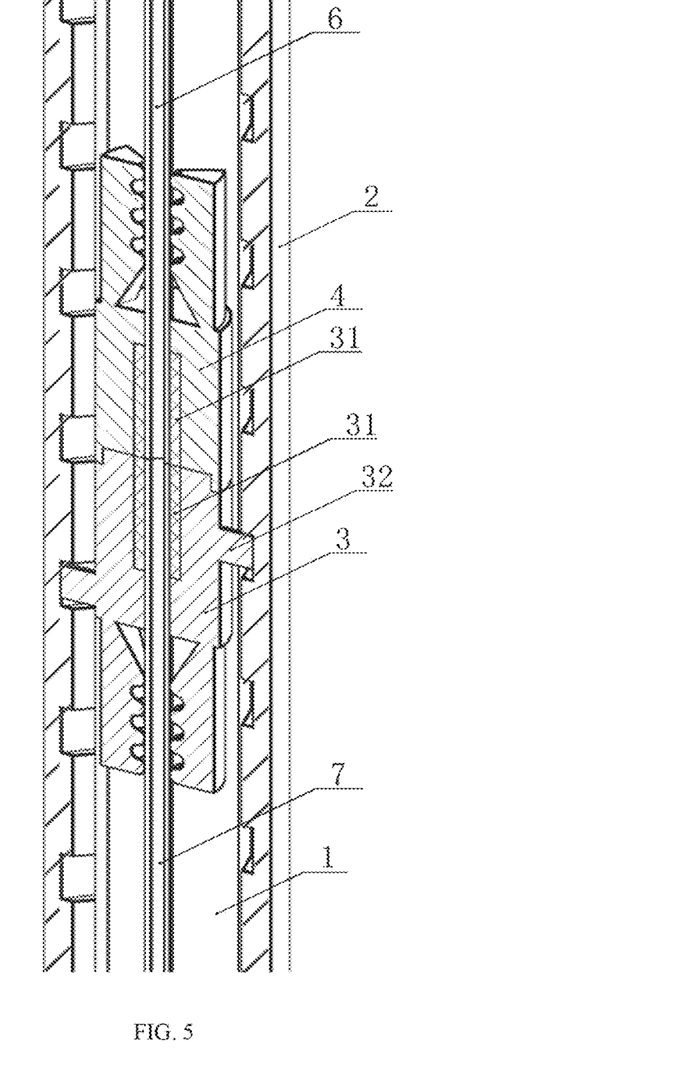
FIG. 5 is a partial enlarged sectional view of the portable immunosensor of the present invention.

Referring to FIG. 5, the clamping device comprises a helix slider 3, a receiving slider 4 and a mechanical splicer 31. The helix slider 3 and the receiving slider 4 are connected in a snap fit, and the mechanical splicer is arranged in the connected helix slider and the receiving slider. A protrusion 32 is provided on an outer wall of the helix slider 3, and a first clamping part is provided at a lower end of the helix slider 3; and a second clamping part is provided at an upper end of the receiving slider 4.

The protrusion 32 slides into the guide groove 12, and then is embedded in the helix groove 21; the protrusion slides up and down in the guide groove 12 to realize the extension and retraction of the optical probe 7.

Two guide grooves 12 are axisymmetrically arranged on the sidewall of the screw cylinder 1.

During use, the optical probe modified by the capture antibody ($Ab_1$) serves as a bio-recognition and signal conversion element and is embedded in the casing. The optical probe has a total length of 12 cm, and the effective length thereof is 10 cm; and the casing has a length of 14.5 cm and an inner diameter of 0.8 cm. The extension and retraction of the pencil-like optical fiber sensor probe can be realized by rotation. During operating, the protrusion of the helix slider slides in the helix groove 21 when the head is held and the casing is rotated, so that the protrusion moves downward along the guide groove 12 to drive the optical probe 7 to extend. In this embodiment, the optical probe is allowed to extend outward for 1 cm when the casing is rotated by 360°, and the remaining part is reserved for following use. So each optical probe can realize 10 immunoassays.

Example 3

In this embodiment, performance testing for the portable immunosensor are illustrated.

1. Characterization of the Portable Immunosensor (PPS Platform)

(1) Reproducibility of the Portable Immunosensor

Figure 8A:
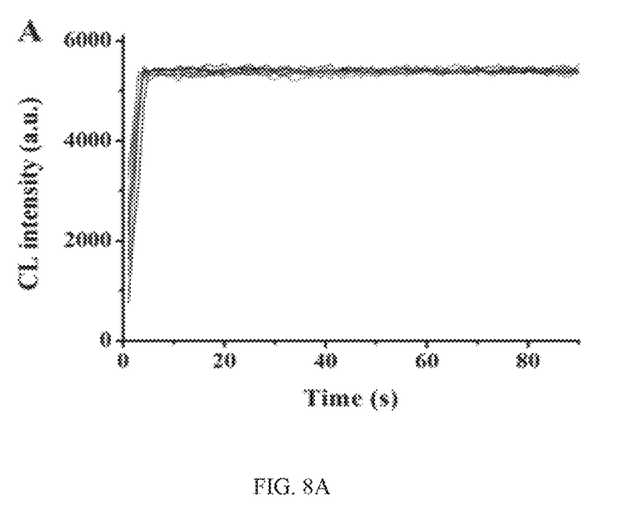
FIG. 8A is a graph showing 10 continuous measurement results on a standard PCT solution using an optical probe.

The optical probe of the immunosensor of the present invention had an effective length of 10 cm. 1 cm was used for each measurement, and then the used part was cut out, and the unused part was rotated for 1 cm for the next measurement. One optical probe was used for 10 parallel determinations of the PCT standard (10 ng/mL). As shown in FIG. 8A, the relative standard deviation (RSD) thereof was less than 5%, indicating that the PPS platform had good reproducibility. Meanwhile, each optical probe can perform 10 analysis processes, which reduces the experimental cost and avoids frequent replacement of probes.

(2) Stability of the Portable Immunosensor

Figure 8B:
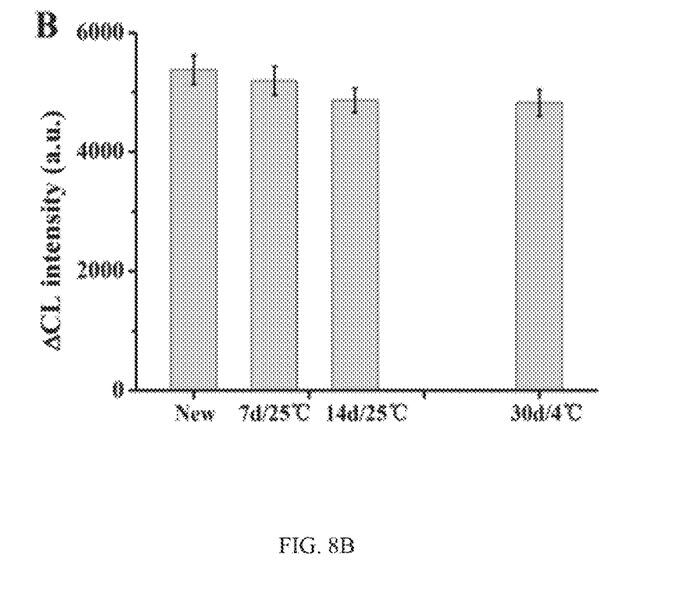
FIG. 8B shows the storage stability of the optical probe under different conditions.

The storage stability of the sensor should be taken into consideration in practical applications. As shown in FIG. 8B, when the sensor probe was stored at room temperature, it maintained 95% of the original response after stored for 7 days, and it still maintained 90% of the original response after stored for 14 days. When the sensor probe was stored in a refrigerator at 4° C. for 30 days, it still maintained 90% of the original response. Therefore, the sensor probe has a good storage stability, so the sensor is suitable for point-of-care test.

2. Sensitivity Testing

Figure 9:
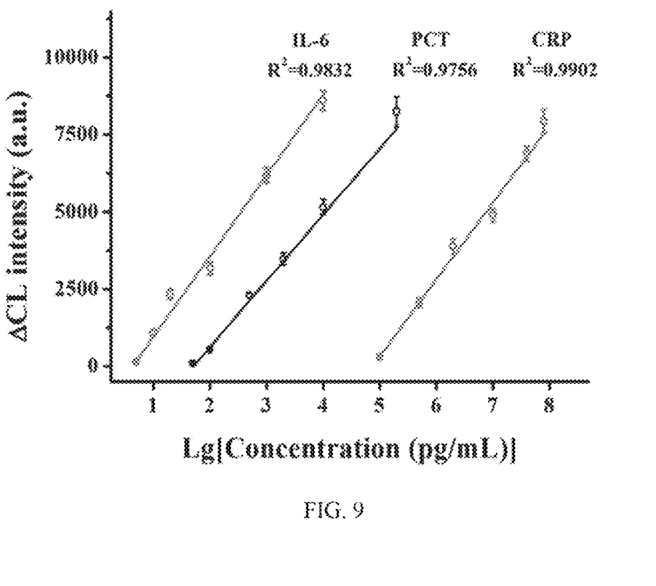
FIG. 9 shows standard curves of IL-6, PCT and CRP measured by the chemiluminescent immunosensor of the present invention.

The sensitivity of the PPS platform was observed under optimum experimental conditions: for IL-6, concentrations of the capture antibody and the detection antibody were 40 μg/mL and 20 μg/mL respectively; for PCT, concentrations of the capture antibody and the detection antibody were 20 μg/mL and 10 μg/mL; for CRP, concentrations of the capture antibody and the detection antibody were 10 μg/mL and 5 μg/mL, respectively; the concentration of streptavidin was 1.25 μg/mL, and the molar ratio of streptavidin to biotinylated horseradish peroxidase was 1:4. Three inflammatory markers (IL-6, PCT and CRP) were measured based on different concentrations (IL-6: 5, 10, 20, 100, 1000, 10000 pg/mL; PCT: 0.05, 0.1, 0.5, 2, 10, 200 ng/mL; CRP: 0.1, 0.5, 2, 10, 40, 80 μg/mL), and a graph showing the chemiluminescence intensity of the markers as a function of concentration is plotted. As shown in FIG. 9, the chemiluminescent signal and the logarithm of the sample concentrations have a substantially linear relationship within concentration ranges of IL-6 (5-10,000 pg/mL), PCT (0.05-200 ng/mL) and CRP (0.1-80 μg/mL). The results showed that the sensor has a sufficiently high sensitivity and a sufficiently wide linear range.

Example 4

1. Testing Method

Figure 7A:
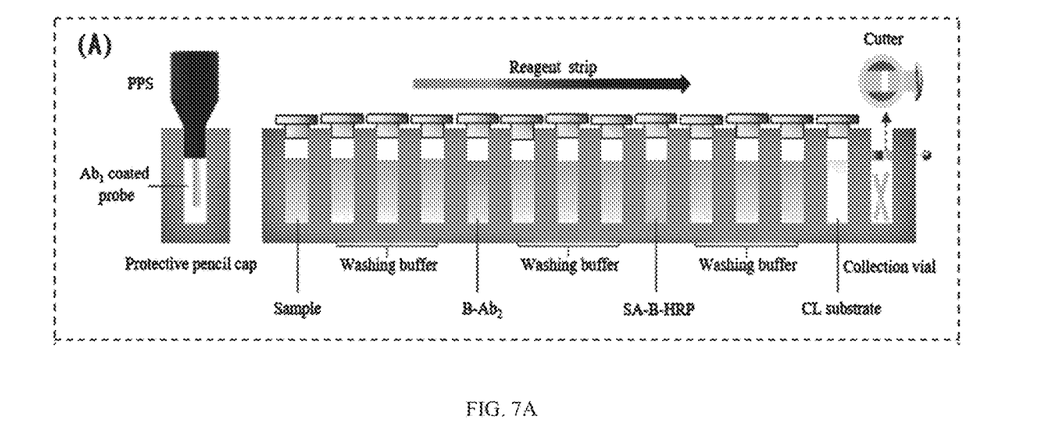
FIGS. 7A-B show the reaction schemes during the PPS platform testing using the portable immunosensor of the present invention.
Figure 7B:
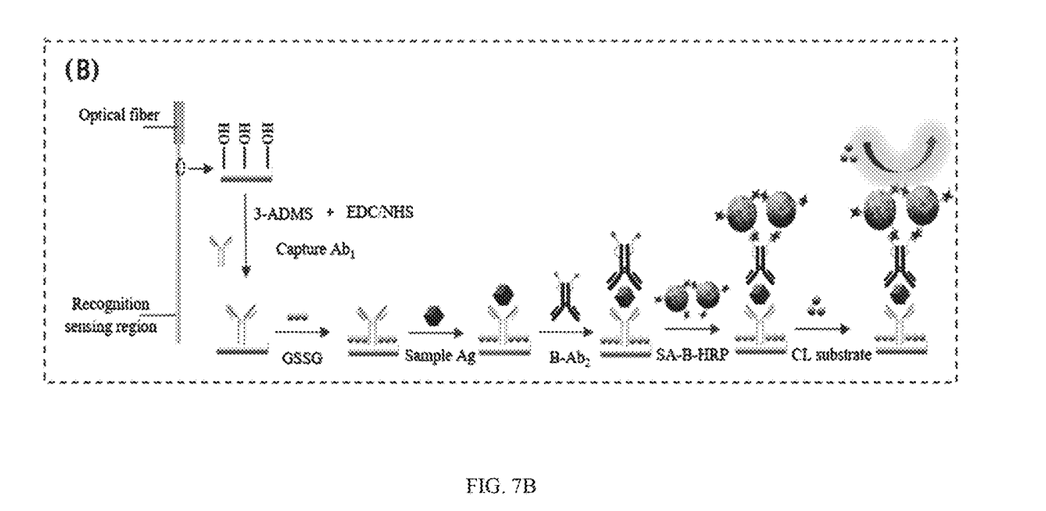

The inflammatory markers interleukin-6 (IL-6), procalcitonin (PCT) and C-reactive protein (CRP) in human serum samples were used as samples for detection. Referring to FIGS. 7A-B, the specific steps were described as follows.

1) The optical probe was rotated to extend outward for 1 cm, and was inserted into the sample reagent container to be incubated at 37° C. for 30 min to capture the target antigen through $Ab_1$ on the sensor probe; after washed three times with PBST, the probe was inserted into the B-$Ab_2$ reagent container to be incubated at 37° C. for 30 min; and then the probe was washed three times with PBST.

2) The optical probe combined with B-$Ab_2$ was inserted into SA-B-HRP reagent container at 37° C. for 30 min, and unbound complexes were washed away with PB ST.

3) The optical probe was placed in a dark reagent container containing the chemiluminescent substrate to generate chemiluminescent signals. The chemiluminescent signals were collected by the compact battery-powered sensitive photon counting detector and analyzed by the screen-touch computer.

4) The concentrations of IL-6, PCT and CRP in the sample were calculated from the measured chemiluminescent intensities, according to respective standard curves.

2. Interference Test

Figure 10A:
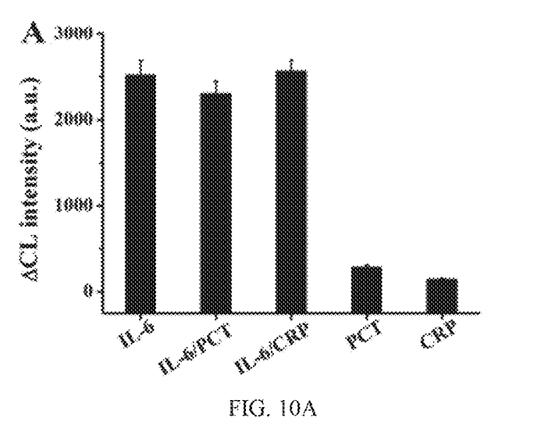
FIGS. 10A-C are charts showing the specificity evaluation for the portable immunosensor of the present invention.
Figure 10B:
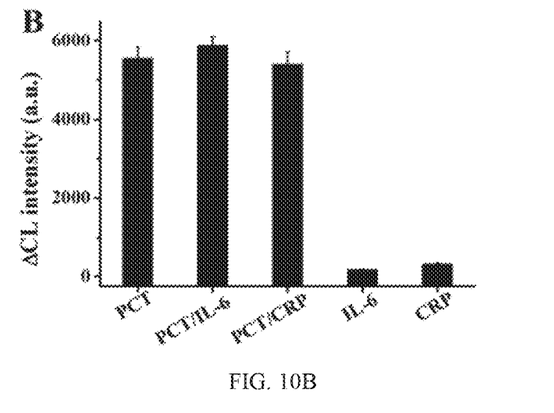
Figure 10C:
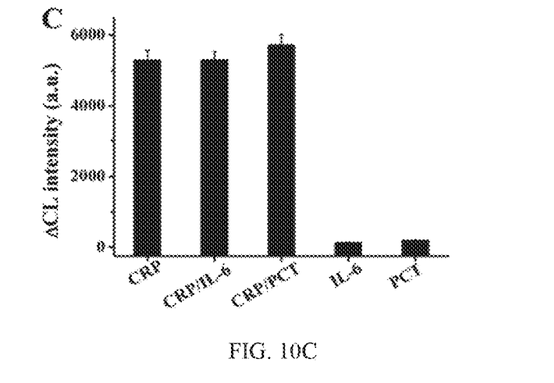

In order to verify the analytical performance of the sensor in practical samples, a study over its selectivity was conducted. The specificity of the sensor was evaluated by mixing the target molecule with interference protein, which indicated that only the target biomarker induced a significant chemiluminescent signal, and the effect of the interference protein on the signal intensity was negligible (FIGS. 10A-C). Spiked CRP (0, 0.2, 10.0 and 50 μg/mL), PCT (0, 0.1, 10 and 100 ng/mL) and IL-6 (0, 10, 500 and 5000 pg/mL) in human serum were also tested. As can be seen from Table 1, the three substances had high recovery percentage (CRP: 90%-107.5%; PCT: 93.5%-107.5%; IL-6: 97.8%-105.8%), indicating that this method can be used to detect infectious disease markers in human serum samples and had good detecting effect. In addition, the relative standard deviations (RSD) were all less than 15%, indicating that the method had good reproducibility.

TABLE 1

Recovery percent of IL-6, PCT and CRP analyzed by PPS platform (n = 3)

| Samples | Spiked value | Measured value | Recovery (%) | RSD (%) |
|---|---|---|---|---|
| IL-6 (pg/mL) | 0 | 58.4 | — | 9.9 |
| | 10.0 | 68.2 | 97.8 | 10.9 |
| | 500.0 | 576.2 | 103.6 | 5.0 |
| | 5000.0 | 5347.1 | 105.8 | 12.2 |
| PCT (ng/mL) | 0 | 3.6 | — | 8.1 |
| | 0.1 | 3.7 | 93.5 | 5.2 |
| | 10.0 | 14.3 | 107.5 | 13.2 |
| | 100.0 | 99.1 | 95.6 | 10.0 |
| CRP (μg/mL) | 0 | 7.9 | — | 4.4 |
| | 0.2 | 8.1 | 92.8 | 6.7 |
| | 10.0 | 18.7 | 107.5 | 13.1 |
| | 50.0 | 52.9 | 90.0 | 7.5 |

3. Detection of Practical Samples

Figure 11A:
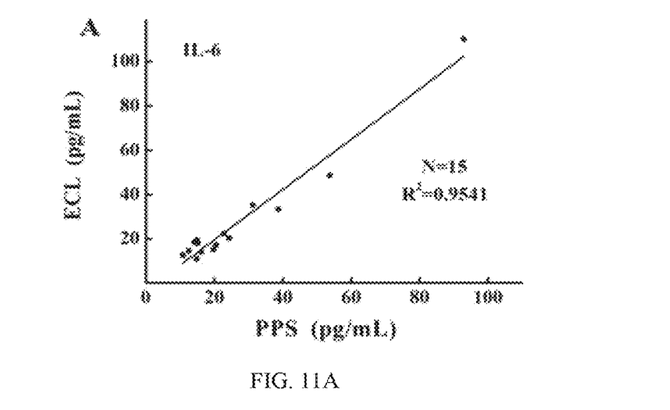
FIGS. 11A-C show the testing results of human serum samples measured by using the portable immunosensor of the present invention and clinical methods.
Figure 11B:
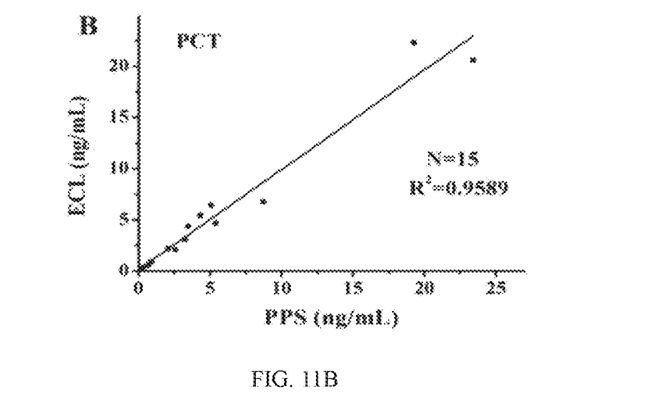
Figure 11C:
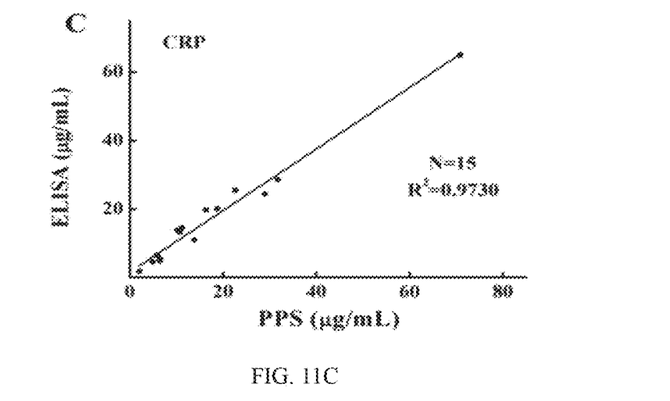

In order to verify the clinical application of the sensor, this method was used to detect IL-6, PCT and CRP samples in 15 human serums. As shown in FIGS. 11A-C, the analysis results were found to have high accuracy when the analysis results of the sensor and results of the clinical methods were compared. The results showed that the sensors of the present invention can realize high-precision analysis on various targets in practical samples. Therefore, the sensor of the present invention has potential application value in point-of-care diagnoses for infectious diseases.

We claim:

1. A pencil-like optical fiber sensor probe, comprising:
an inner tube;
a casing;
a clamping device;
an optical fiber;
and an optical probe;
wherein the inner tube comprises a head, a screw cylinder and a tail cap; a fixing part is provided at an upper end of the screw cylinder, and a guide groove is provided on a sidewall of the screw cylinder; and the tail cap is fixed to the fixing part;
the casing is sheathed on the screw cylinder, and a helix groove is provided on an inner wall of the casing;
the clamping device is arranged in the screw cylinder; a protrusion is provided on an outer wall of the clamping device; the protrusion is mounted in the guide groove and then is embedded into the helix groove; and
the clamping device comprises a helix slider, a receiving slider and a mechanical splicer; the helix slider and the receiving slider are connected in a snap fit; the mechanical splicer is arranged in the connected helix slider and the receiving slider, and the protrusion is provided on an outer wall of the helix slider.
the optical fiber and the optical probe are coaxially connected in the clamping device.

2. The pencil-like optical fiber sensor probe of claim 1, wherein the casing is made of a light screening material.

3. The pencil-like optical fiber sensor probe of claim 1, wherein a first clamping part is provided at a lower end of the helix slider, and a second clamping part is provided at an upper end of the receiving slider.

4. The pencil-like optical fiber sensor probe of claim 3, wherein two guide grooves are axisymmetrically arranged on the sidewall of the screw cylinder.

5. A portable immunosensor, comprising:
the pencil-like optical fiber sensor probe of claim 1;
an immersion immune response reagent strip;
a screen-touch computer;
a compact battery-powered sensitive photon counting detector; and
a case;
wherein the pencil-like optical fiber sensor probe, the immersion immune response reagent strip, the screen-touch computer and the compact battery-powered sensitive photon counting detector are arranged in the case; the pencil-like optical fiber sensor probe, the compact battery-powered sensitive photon counting detector and the screen-touch computer are sequentially connected; and the compact battery-powered sensitive photon counting detector is arranged in a dark place.

6. The portable immunosensor of claim 5, wherein the pencil-like optical sensor probe, the immersion immune response reagent strip and the touch-screen computer are installed at an upper layer of the case, and the compact battery-powered sensitive photon counting detector is sealed at the dark place which is located at a bottom of the case.

7. Use of the portable immunosensor of claim 6 in the detection of an inflammatory marker.

8. The use of claim 7, wherein the inflammatory marker is interleukin-6, procalcitonin and/or C-reactive protein.

* * * * *